United States Patent [19]

Kunstle et al.

[11] 4,008,260
[45] Feb. 15, 1977

[54] PROCESS FOR PREPARING COBALT(III)ACETYLACETONATE

[75] Inventors: Gerhard Kunstle, Raitenhaslach; Herbert Siegl, Haiming, both of Germany

[73] Assignee: Wacker-Chemie GmbH, Munich, Germany

[22] Filed: Mar. 24, 1975

[21] Appl. No.: 561,463

[30] Foreign Application Priority Data

Apr. 29, 1974 Germany .......................... 2420691

[52] U.S. Cl. .......................... 260/439 R; 260/429 J
[51] Int. Cl.$^2$ .......................... C07F 15/06
[58] Field of Search .................... 260/439 R, 429 J

[56] References Cited

UNITED STATES PATENTS 3,474,464  10/1969  Matthews ...................... 260/439 R

OTHER PUBLICATIONS

Bryant et al., Inorganic Synthesis, vol. 5, pp. 188–189 (1957).
Chemical Abstracts, vol. 22, 3854–3855 (1928).
Chemical Abstracts, vol. 79, 10362q (1973).
Chemical Abstracts, vol. 54, 20436c (1960).
J. Phip. Chem. vol. 64, pp. 660–664 (1960).

*Primary Examiner*—Helen M. S. Sneed
*Attorney, Agent, or Firm*—Allison C. Collard

[57] ABSTRACT

Process for preparing cobalt(III)acetylacetonate comprising the steps of adding to cobalt(II)acetylacetonate in an organic solvent, at least the stoichiometric amount of acetylacetone, oxidizing with an excess of hydrogen peroxide, and separating the obtained cobalt-(III)acetylacetonate by cooling and or concentration of the solution. The product obtained after drying is analytically pure and may be directly used as a catalyst for many chemical reactions, such as dimerizations, oligomerizations and polymerizations, oxidations and hydrogenations of olefins and many more.

5 Claims, No Drawings

PROCESS FOR PREPARING COBALT(III)ACETYLACETONATE

The present invention relates to a process for preparing cobalt(III)acetylacetonate.

It is known to prepare cobalt(III)acetylacetonate by reacting an aqueous suspension of freshly precipitated cobalt sesquioxide with acetylacetone. However, the product obtained is not of uniform structure and requires an additional purification which results in a decrease in yield.

It is an object of the present invention to provide a process for preparing cobalt(III)acetylacetonate which leads to an analytically pure product obtained in high yield. According to the invention, this object is accomplished by adding to cobalt(III)acetylacetonate in an organic solution, at least the stoichiometric amount of acetylacetone, oxidizing the obtained reaction product with an excessive amount of hydrogen peroxide, and separating as end product, cobalt(III)acetylacetonate by cooling and/or concentrating the solution.

It was surprising to find, in contrast to the existing literature, that a product was thereby obtained having a completely uniform structure, which does not require a subsequent purification.

In general, the procedure is carried out by dissolving cobalt(II)acetylacetonate in an organic solvent and adding to the solution, while stirring, at least the stoichiometric amount, preferably an excess of 5–10 molar %, of acetylacetone, at a temperature of 20° – 60° C, and preferably 30° – 50° C.

The cobalt(II)acetylacetonate can be prepared according to any of the processes known from the literature, or by adding acetylacetone to an aqueous solution of cobalt dichloride with adjustment of the pH value to 7 – 8 by adding ammonia.

The organic solvents which may be used have to be inert to the reaction and primarily resistant to oxidation in the solvent chosen, the starting materials have to be readily soluble, but on the other hand, the end product should be easy to isolate. Examples are, e.g. aromatic hydrocarbons, such as benzene or toluene, chlorinated hydrocarbons, e.g. carbon tetrachloride or tetrachloroethane, but preferably alcohols, e.g. methanol, ethanol, propanols or butanols.

To the clear solution containing cobalt(II)acetylacetone and acetylacetone, hydrogen peroxide is subsequently added, preferably as aqueous solution of 25 – 30% in an excess amount of 1.5 to 2.5 mols. The rate at which addition occurs should be so adjusted that the temperature does not exceed 100° C, preferably 80° C, the oxidation being thus carried out in a temperature range of 20 – 100° C, preferably 40°– 80° C. As a rule, a rapid and complete mixing is achieved by using a suitable stirring device. A quantitative reaction is indicated by a clear green coloring of the solution. If this should not occur, it may be necessary to add more hydrogen peroxide until all the cobalt(II)salt is oxidized.

The reaction mixture is then heated to refluxing, in order to boil off excessive hydrogen peroxide. Upon subsequent cooling, cobalt(III)acetylacetonate is precipitated and separated, washed with cold solvent, and dried at a temperature of 20° – 100° C, and preferably 40° – 80° C, and at a reduced pressure of preferably 5 – 30 torr.

If the operation is carried out discontinuously the mother liquor is worked up in a conventional manner or simply added to the next batch. In continuous operation, the mother liquor is preferably recycled and the precipitated cobalt(III)acetylacetonate continuously separated and discharged.

The analytically pure cobalt(III)acetylacetonate obtained by the process according to the invention in a high yield, can be directly used in a large number of chemical reactions: For instance, as catalyst in the dimerization, oligomerization, or polymerization of olefins and aldehydes, e.g. dimerization of isoprene or ethylene yielding 1,2-dimethyl-4-vinyl-1-cyclohexene or n-butene, respectively, wherein high selectivity is achieved; in the oligomerization of butadiene and the polymerization of formaldehyde; in the hydroformylation of olefins, unsaturated aldehydes or ketones, e.g. cyclopentene to form cyclopentane aldehyde, in oxidation reactions, e.g. forming acetone from iso-propanol, and in hydrogenations of olefins, aromatics, nitro compounds and ketones.

In the following, the process of the invention will be more fully described by an example, but it should be understood, that this is given by way of illustration and not of limitation.

EXAMPLE 582.5 grams cobalt(II)acetylacetonate, made from cobalt dichloride and acetylacetone by reaction with ammonia, having a water content of 11.7% by weight, corresponding to 509.6 grams of the anhydrous compound, were dissolved in 2 liters of methanol at room temperature and thereto 210 grams of acetylacetone were added at 35° C, while stirring. Subsequently, to the clear solution 150 grams hydrogen peroxide of about 30% were added within 8 minutes, which led to an increase in temperature of the solution to 65° C. The solution was then stirred at 65° C for about 30 minutes, and another 80 grams of about 30% hydrogen peroxide were added until the solution had turned to a clear green color. Thereafter, the reaction mixture was heated to reflux for one hour, cooled to 3° C, and the precipitated cobalt(III)acetylacetonate filtered and washed with 100 ml of cold methanol. After drying at 5 torr/80° C for 5 hours, 539 grams cobalt(III)acetylacetonate were obtained (corresponding to 75.7% of the theoretical). The product was black and shining, and of finely-crystalline structure, and having a water content of less than 0.05% by weight.

In order to determine the yield, in a second batch, the mother liquor obtained in the first batch was used as solvent; otherwise the weight of the reactants and the procedure were completely analogous to the above example. Obtained were 630 grams, corresponding to 88.4% of the theoretical, black shining cobalt(III)acetylacetonate of finely crystalline structure having a water content of less than 0.05% by weight.

When the mother liquor was up in the usual manner, a further amount of 83 grams cobalt(III)acetylacetonate with a water content of < 0.05% by weight was obtained.

| Analysis | C | H | Co |
|---|---|---|---|
| Calculated | 50.58 | 5.90 | 16.55 |

| Analysis | | | |
|---|---|---|---|
| Found | 50.59 | 6.14 | 16.61 |

What is claimed is:

1. A process for the preparation of cobalt (III) acetylacetonate having a black fine crystalline structure and a water content of less than 0.05% by weight, comprising the steps of:
   a. dissolving cobalt (II) acetylacetonate in an organic solvent;
   b. adding to the solution at a temperature between about 20° and about 60° C at least the stoichiometric amount of acetylacetone to provide an additional mol thereof;
   c. adding aqueous 25% to 35% hydrogen peroxide solution in an excess amount of 1.5 to 2.5 mols, with stirring, at a temperature between about 20° and 100° C until oxidation is complete; and
   d. boiling off excess hydrogen peroxide, cooling the solution, and recovering the precipitated solid cobalt(III)acetylacetonate therefrom.

2. The process according to claim 1 wherein in step (b) the acetylacetone is added in an excess of 5 to 10 molar % of the stoichiometric amount.

3. The process according to claim 1 wherein the cobalt(III)acetylacetonate is separated by concentrating the solution.

4. The process according to claim 1 wherein the oxidation is carried out at a temperature of 40° to 80° C.

5. The process according to claim 1 comprising the additional step of drying the separated cobalt(III)acetylacetonate at a temperature of 20° to 100° C under reduced pressure.

* * * * *